United States Patent [19]

Kang

[11] Patent Number: 4,896,432
[45] Date of Patent: Jan. 30, 1990

[54] STATURE MEASURING APPARATUS

[75] Inventor: Dong M. Kang, Seoul, Rep. of Korea

[73] Assignee: Korea Measurers Co., Ltd., Busan, Rep. of Korea

[21] Appl. No.: 260,441

[22] Filed: Oct. 20, 1988

[30] Foreign Application Priority Data

Dec. 4, 1987 [KR] Rep. of Korea ............... 21433/1987

[51] Int. Cl.$^4$ .............................................. G01B 3/08
[52] U.S. Cl. ...................................... 33/768; 33/770; 33/769
[58] Field of Search ............ 33/138, 139, 140, 169 R, 33/761, 768, 769, 770, 832

[56] References Cited

U.S. PATENT DOCUMENTS 4,638,563 1/1987 Buniff .............................. 33/169 R

FOREIGN PATENT DOCUMENTS 1320169 1/1963 France ................................. 33/138
54104 4/1980 Japan ..................................... 33/138

Primary Examiner—Harry N. Haroian
Attorney, Agent, or Firm—Flynn, Thiel, Boutell & Tanis

[57] ABSTRACT

A stature measuring apparatus detachably mounted on a wall surface so that it may be installed only when stature is going to be measured. A fixing and holding plate 10 is releasably attached to a tape head 8 to which an end of the measuring tape is secured. A measuring tape body housing 1 has a switch button plate 7 on the bottom surface of a rectangular measuring plate 6 so that, as soon as the switch plate 7 touches the top of the head of a man, the switch plate 7 may be pressed, and a light emitting diode is lit and a melody sounds simultaneously. Then an observer can read out indicia on the measuring tape through a view window 4 without needing to be concerned about whether or not the measuring plate 6 is contacting the mans head firmly. The apparatus can be detached easily when it is not in use.

8 Claims, 4 Drawing Sheets

STATURE MEASURING APPARATUS

CROSS REFERENCE TO RELATED APPLICATION

This application is related in subject matter to my pending design application Ser. No. 163 464, filed Mar. 3, 1988.

FIELD OF THE INVENTION

The present invention relates to a stature measuring apparatus which can measure both the stature and the sitting height by setting it simply on a wall of the room at about 2 meters high from the floor level.

BACKGROUND OF THE INVENTION

Conventionally, a typical stature measuring apparatus includes a rectangular pole standing vertically on a horizontal base plate, some scales are calibrated thereon, and a measuring square bar, mounted perpendicularly to the rectangular pole, slidingly mounted on a surface of the scaled rule of the pole so that the height between the base plate and the perpendicular measuring bar can be measured by reading the scale of the stopped position of the measuring bar.

Another conventional height measuring device is composed of two parts, one part being a measuring tape head formed integrally with a holding plate which may be fixed directly on a wall, an end of the measuring tape being secured in it, and the other part being a measuring tape body housing which has a measuring plate on the bottom surface and a tape winding contained therein. Heretofore, there has been the disadvantage that, because the tape head and measuring tape body housing have to be arranged constantly on a wall of the room even when the stature would not be measured, the available space in the room may already be occupied, and the appearance of the wall may be marred by its presence. Furthermore, there has been also the disadvantage that an observer must confirm directly with the eyes and sense whether or not the bottom surface of the measuring tape body housing touches correctly onto the top of the head of a man to be measured for every measuring case.

Therefore, to solve the problems as above described, an object of the present invention is to provide a stature measuring apparatus which is detachable from the wall easily for when the apparatus is not in use so that the wall may be kept clean without any unnecessary protruding articles and also the apparatus may be stored safely within a storage area without suffering any damage.

Another object of the present invention is to provide a stature measuring apparatus in which the direct confirmation with the eyes, namely, whether or not the bottom surface of the measuring tape body housing touches correctly onto the top of the head of a man to be measured may not be required, due to the generation of a sound or a melody or a lighting of a lamp automatically as soon as the bottom surface of the measuring tape body housing touches the top of the head of a man to be measured.

SUMMARY OF THE INVENTION

An aspect of the present invention is that the tape head in which an end of the measuring tape is secured can be secured to or detached from a fixed relation with a fixing and holding plate which is fixed permanently on a wall so that the measuring apparatus can be mounted only when a stature measurement may be required or else detached therefrom.

Another aspect of the present invention is that the measuring tape body housing may be formed, for instance, with a dolphin-shaped external appearance, and may be integrally fixed on a rectangular measuring plate, and the rolled measuring tape is contained within the dolphin-shaped housing. The housing may be suspended from the tape head on a wall, and a switch plate is arranged on the bottom surface of the rectangular measuring plate so that, when a stature is going to be measured, as soon as the aforementioned switch plate touches the top of the head of a man to be measured, the predetermined melody stored in a memory element may sound, at the same time, a light emitting diode may light up the eyes of the dolphin of the measuring tape body housing so that one can measure the stature merely by reading out the scale number of the base line through the transparent view window.

DETAILED DESCRIPTION OF THE INVENTION

Figure 1:
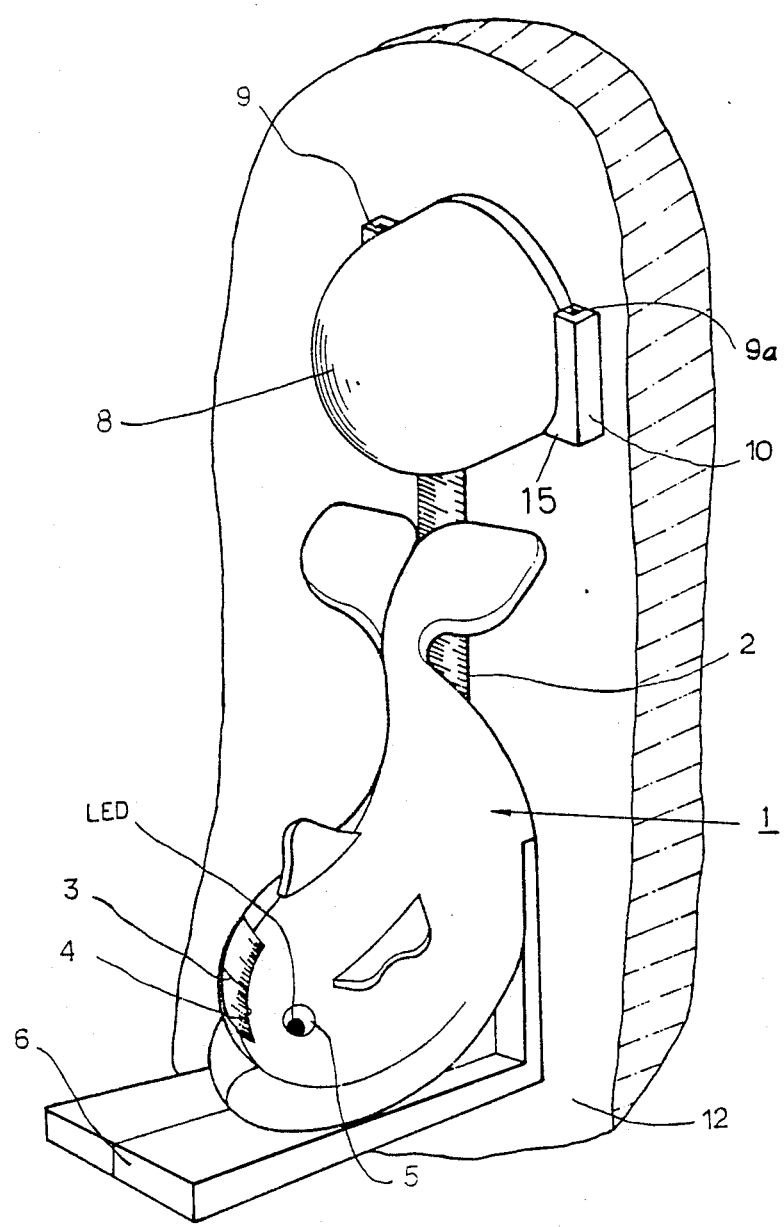
FIG. 1 shows a perspective view illustrating the set condition of a measuring apparatus according to the present invention.

The present invention will be described in detail with reference to the drawings, and in the different figures, like reference numerals denote corresponding elements.

In FIG. 1, the numeral 1 is a dolphin-shaped measuring body housing which contains a roll up device for a measuring tape 2, a transparent view window 4 on which a base or reference line 3 is marked to facilitate a read out of the scale indicia on the measuring tape 2 which is guided past the window 4 located in front of the lower portion of this measuring tape body housing 1. Two eyes 5 are provided on the dolphin which include light emitting diodes LED. The eyes are provided on opposite sides of the transparent view window 4.

The numeral 6 is a rectangular measuring plate which is integrally mounted with the bottom of the measuring tape body housing 1. A switch button plate 7 is arranged on the bottom surface of this rectangular measuring plate 6, as shown in FIG. 2.

Figure 2:
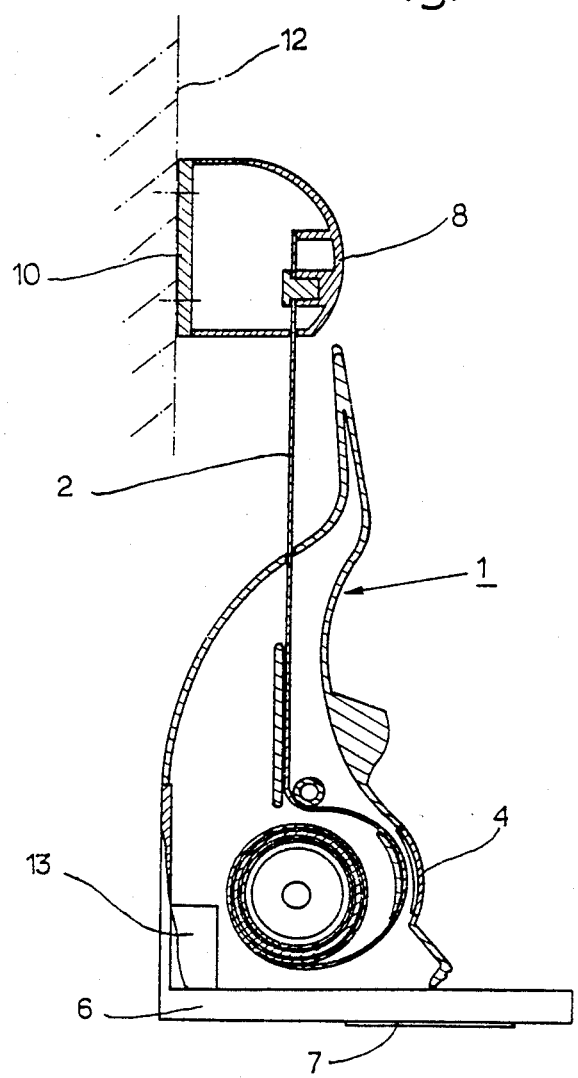
FIG. 2 is a central longitudinal cross sectional view showing the set condition of a measuring apparatus according to the present invention.
Figure 3:
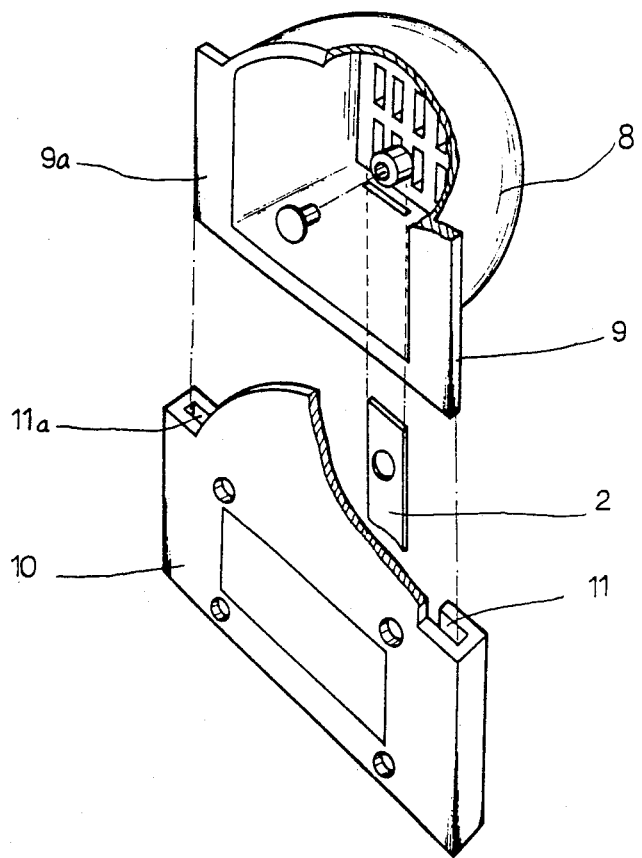
FIG. 3 is an exploded perspective view of a fixing and holding device of a partly removed tape head.

In FIGS. 2 and 3, the numeral 8 is a measuring tape head to which an end of the measuring tape 2 is inserted and secured therein. The measuring tape head 8 is formed as a hemisphere which has a cut out along its bottom portion. The hemisphere also has sliding insert plates 9, 9a integrally formed along both sides of the hemisphere.

The numeral 10 is a fixing and holding plate having grooves 11, 11a formed along both sides thereof so that the aforementioned sliding insert plates 9, 9a on the measuring tape head 8 may be inserted and held therein. The lower part of the grooves 11, 11a of the fixing and holding plate 10, including a portion 15 (FIG. 1) of the fixing and holding plate 10 adjacent the grooves 11,11a, converge gradually toward each other such that the curvature of the lower part of the measuring tape head 8 and converging portions 15 come in contact with each other. The fixing and holding plate 10 is fixed to a wall 12 or the like with bolts or screws, as shown in FIGS. 1, 2 and 4.

Figure 4:
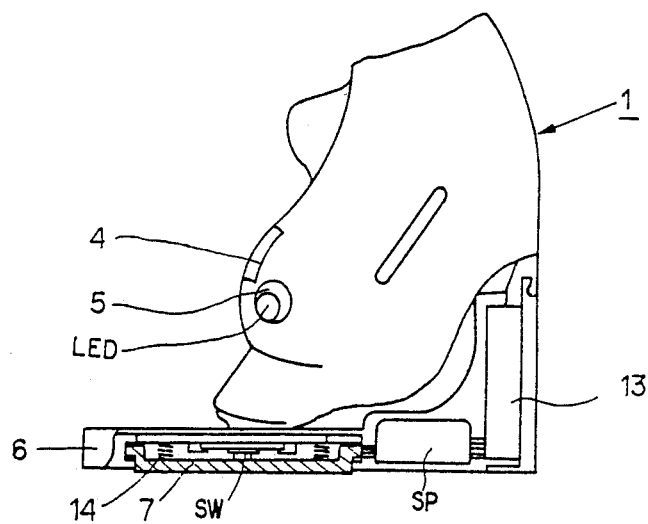
FIG. 4 is a side view of the present invention with the contacting portion being partly removed.
Figure 5:
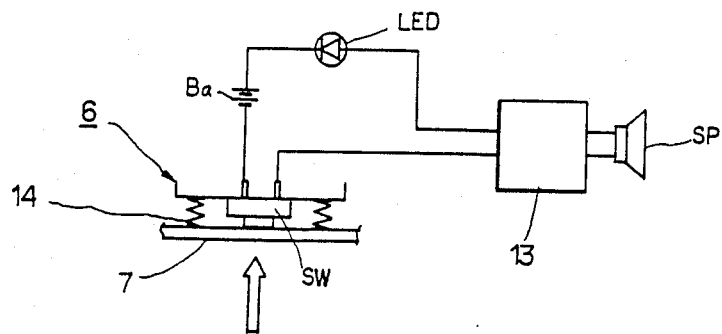
FIG. 5 shows the wiring diagram of the present invention.

In FIGS. 4 and 5, the numeral 13 is a melody box, and the numeral 14 is a resilient coil spring which is disposed between the switch button plate 7 and the rectangular measuring plate 6. The reference code SP is a loud speaker, and the reference code SW is a switch which is disposed in a recess in the bottom surface of the measuring plate 6 and operated by the switch button plate 7.

OPERATION

The operation and the effectiveness of the present invention constructed such as above will be explained as follows:

At first, the bottom of the rectangular measuring plate 6 of the measuring tape body housing 1 may be placed adjacent the base board of a floor, then the fixing and holding plate 10, with the assembled measuring tape head 8, may be pulled straight up the wall until the 2 meter scale or indicia on the measuring tape 2 corresponds or is aligned with the base line in the middle of the transparent view window 4 in front of the measuring tape body housing 1. After disassembling the measuring tape head 8 from the fixing and holding plate 10, the fixing and holding plate 10 may be fixed to the wall 12 with bolts or screws.

Thereafter, both sliding insert plates 9, 9a of the measuring tape head 8 may be inserted into the grooves 11, 11a of the fixing and holding plate 10 only when the stature is desired to be measured. The rectangular measuring plate 6 of the measuring tape body housing 1 may be pulled down gradually until the bottom of the rectangular measuring plate touches the top of the head of a man to be measured. As soon as the switch button plate 7 within the bottom surface of the rectangular measuring plate 6 touches the top of the head of a man, the switch SW will close to the ON condition and accordingly a melody which is stored in the melody box 13 may be sounded through the loud speaker SP, at the same time, the light emitting diode LED forming the eyes on the dolphin-shape may be lit as a desired color, such as a red light or a blue light, so that an observer can easily recognize that the measuring plate 6 has touched firmly the top of the head of a man to be measured and so that the stature of a man to be measured can be measured by just reading out the scale indicia on the tape ruler 2 showing through the transparent view window 4 in front of the measuring tape body housing 1.

After the stature of a man to be measured is measured, because the force which is pressing in the switch button plate 7 within the bottom surface of the rectangular measuring plate 6 may be removed, the switch button plate 7 may be returned to the original position by the resilient coil spring 14 so that it returns to the ready condition for a further measurement. At the same time, the switch SW will open to the OFF condition and the operation of the melody box will be stopped and also the light emitting diode LED will be turned OFF.

According to the present invention, as described above, the measuring tape head 8 can be removed easily from the fixing and holding plate 10 whenever a measuring task is not needed so that the space within a room can be widely utilized. More specifically, the lower exterior portion 15 of the part defining the grooves 11, 11a of the fixing and holding plate 10 converge inwardly slightly and conform to the curvature of the hemisphere shaped tape head 8, so that the measuring tape head 8 can be held fixedly without falling down from the fixing and holding plate 10 if the insert plates 9, 9a of the tape head 8 are inserted merely into the grooves 11, 11a of the fixing and holding plate 10. In addition, and because the feature of the measuring tape body housing 1 is formed with dolphin-shape, and a melody is sounding through the loud speaker SP and the eyes of the dolphin are lit during the time of measurement, children like to have their stature measured with this apparatus without any hesitation. Therefore, the invention is greatly utilized and with more effectiveness.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. A stature measuring apparatus for measuring stature, comprising:
   a fixing and holding plate adapted to be fixed on a wall;
   a measuring tape head, a measuring tape having an end secured to said measuring tape head, means for releasably securing said measuring tape head to said fixing and holding plate; and
   a measuring tape body housing having a rectangular measuring plate fixed thereto, said measuring tape body housing containing means for rolling up said measuring tape and a window through which said measuring tape can be viewed, at least one light emitting diode and an audible melody mechanism, said measuring plate including a recess formed in a bottom surface thereof, said recess having an internal switch mounted therein, a switching button plate covering said recess, power supply means for driving said light emitting diode and said audible melody mechanism, said switch being operable to operably connect said power supply means to said light emitting diode and said audible melody mechanism, said switch button plate being coupled with said switch so that, when said switch button plate is pressed, said switch is operated and said light emitting diode is lit and said audible melody mechanism is operated simultaneously, said lit diode and said audible melody mechanism indicating that said measuring plate is firmly engaged with an object the stature of which is being measured.

2. The stature measuring apparatus according to claim 1, wherein said tape body housing has the appearance of a dolphin, and wherein two said light emitting diodes are provided and are located so as to define the eyes of the dolphin, said window being oriented between said two eyes.

3. The apparatus according to claim 1, wherein said releasably securing means includes one of said measuring tape head and said fixing and holding plate having associated therewith means defining an insertion member extending therefrom, and the other of said measuring tape head and said fixing and holding plate having associated therewith means for slidably receiving said insertion member.

4. The apparatus according to claim 3, including stop means for capturing said insertion member in said receiving means.

5. The apparatus according to claim 4, wherein said insertion member defining means includes at least one insert plate, and wherein said receiving means includes means defining at least one groove for receiving an edge of said insert plate.

6. The apparatus according to claim 5, including a pair of said insert plates affixed to said measuring tape head, said insert plates extending along respective sides of said measuring tape head, said fixing and holding plate having a pair of mutually facing said grooves formed thereon for slidably receiving said insert plates to support said measuring tape head therebetween.

7. The apparatus according to claim 6, wherein said stop means includes respective portions of said fixing and holding plate adjacent said grooves being slightly curved so as to gradually converge toward each other, said portions of said fixing and holding plate abutting said measuring tape head when said insert plates are received in said grooves.

8. The apparatus according to claim 7, wherein said measuring tape head has a generally curved contour, said curved portions of said fixing and holding plate conforming with said measuring tape head contour and fitting around a part of said measuring tape head contour when said insert plates are received in said grooves.

* * * * *